United States Patent
Philip et al.

(10) Patent No.: US 11,013,748 B2
(45) Date of Patent: May 25, 2021

(54) BUDESONIDE PRODRUG

(71) Applicant: University of Nizwa, Birkat Al-Mauz (OM)

(72) Inventors: Anil K. Philip, Birkat Al-Mauz (OM); Betty Annie Samuel, Birkat Al-Mauz (OM); Hamna Naseer Al Senani, Birkat Al-Mauz (OM); Afaf Mohammed Weli, Birkat Al-Mauz (OM); Ahmed-Sulaiman Fadhil Al Harrasi, Birkat Al-Mauz (OM); Ahmed bin Khalfan Al Rawahi, Birkat Al-Mauz (OM)

(73) Assignee: UNIVERSITY OF NIZWA, Nizwa (OM)

( * ) Notice: Subject to any disclaimer, the term of this patent is extended or adjusted under 35 U.S.C. 154(b) by 47 days.

(21) Appl. No.: 16/591,940

(22) Filed: Oct. 3, 2019

(65) Prior Publication Data
US 2021/0100818 A1   Apr. 8, 2021

(51) Int. Cl.
*A61K 31/58*   (2006.01)
*A61K 9/48*   (2006.01)

(52) U.S. Cl.
CPC ............. *A61K 31/58* (2013.01); *A61K 9/48* (2013.01)

(58) Field of Classification Search
CPC .............. A61K 2039/505; A61K 45/06; A61K 39/3955; A61K 39/39558; A61K 9/0019; A61K 2039/507; A61K 31/519; A61K 31/573; A61K 9/0053; A61K 2300/00; A61K 31/05; A61K 31/58; A61K 38/00; A61K 9/0014; A61K 9/0073; A61K 9/1617; A61K 2035/124; A61K 2039/5156; A61K 31/145; A61K 31/337; A61K 31/352; A61K 31/4184; A61K 31/42; A61K 31/436; A61K 31/438; A61K 31/44; A61K 31/4439; A61K 31/472; A61K 31/496; A61K 31/55; A61K 31/65; A61K 31/7048; A61K 31/7068; A61K 31/7125; A61K 31/713; A61K 35/12; A61K 35/17; A61K 38/13; A61K 39/0011; A61K 39/085; A61K 47/10; A61K 47/6929; A61K 9/0048; A61K 9/0095; A61K 9/08; A61K 9/5026; A61K 2035/122; A61K 2039/5154; A61K 2039/545; A61K 31/00; A61K 31/047; A61K 31/122; A61K 31/137; A61K 31/138; A61K 31/167; A61K 31/17; A61K 31/19; A61K 31/192; A61K 31/196; A61K 31/215; A61K 31/225; A61K 31/255; A61K 31/341; A61K 31/4035; A61K 31/4045; A61K 31/41; A61K 31/415; A61K 31/416; A61K 31/4162; A61K 31/4166; A61K 31/4174; A61K 31/4178; A61K 31/435; A61K 31/439; A61K 31/4525; A61K 31/454; A61K 31/4545; A61K 31/4709; A61K 31/4725; A61K 31/495; A61K 31/502; A61K 31/5025; A61K 31/505; A61K 31/506; A61K 31/513; A61K 31/517; A61K 31/522; A61K 31/5377; A61K 31/5383; A61K 31/5415; A61K 31/5513; A61K 31/56; A61K 31/568; A61K 31/57; A61K 31/616; A61K 331/662; A61K 31/664; A61K 31/683; A61K 31/7024; A61K 31/7034; A61K 31/7036; A61K 31/7052; A61K 31/7076; A61K 33/06; A61K 33/42; A61K 35/15; A61K 35/28; A61K 36/185; A61K 38/07; A61K 38/08; A61K 38/10; A61K 38/15; A61K 38/16; A61K 38/164; A61K 38/1774; A61K 38/1841; A61K 38/191; A61K 38/195; A61K 38/2006; A61K 38/2013; A61K 38/21; A61K 38/212; A61K 38/28; A61K 38/39; A61K 38/57; A61K 39/00; A61K 39/001104; A61K 39/00111; A61K 39/001112; A61K 39/001113; A61K 39/001119; A61K 39/001124; A61K 39/001129; A61K 39/001168; A61K 39/001171; A61K 39/001186; A61K 39/001188; A61K 39/001195; A61K 39/40; A61K 45/05; A61K 47/12; A61K 47/14; A61K 47/22; A61K 47/44; A61K 47/543; A61K 47/554; A61K 47/643; A61K 47/6803; A61K 47/6817; A61K 47/6849; A61K 47/6851; A61K 48/00; A61K 48/0008; A61K 48/0058; A61K 48/0075; A61K 48/0083; A61K 51/00; A61K 8/0212; A61K 8/027; A61K 8/0275; A61K 8/042; A61K 8/34; A61K 8/361; A61K 8/39; A61K 8/4913; A61K 8/731; A61K 8/9789; A61K 9/0004; A61K 9/007; A61K 9/0075; A61K 9/0078; A61K 9/008; A61K 9/10;
(Continued)

(56) References Cited

U.S. PATENT DOCUMENTS

| 9,707,182 B2 * | 7/2017 | Thennati | A61P 1/04 |
| 2015/0118296 A1 * | 4/2015 | Kulkarni | A61K 9/2846 424/452 |

OTHER PUBLICATIONS

Asymmetric Membrane in Membrane Capsules: A Means for Achieving Delayed and Osmotic Flow of Cefadroxil, Anil K. Philip, Kamla Pathak, Pragati Shakya, ScienceDirect, Jan. 8, 2008.
(Continued)

*Primary Examiner* — Audrea B Coniglio
*Assistant Examiner* — Audrea Buckley (74) *Attorney, Agent, or Firm* — Paul & Paul (57) ABSTRACT

Phase-inverted capsules of a prodrug of budesonide are provided for treatment of bowel diseases.

20 Claims, 6 Drawing Sheets

(58) Field of Classification Search
CPC ...... A61K 9/16; A61K 9/1623; A61K 9/1635; A61K 9/1641; A61K 9/1652; A61K 9/1658; A61K 9/1676; A61K 9/1682; A61K 9/1694; A61K 9/204; A61K 9/2045; A61K 9/2054; A61K 9/4858; A61K 9/4866; A61K 9/5015; A61K 9/5078; A61K 9/5084; A61K 9/5089; A61K 9/5169; A61P 35/00; A61P 11/00; A61P 25/28; A61P 11/06; A61P 21/06; A61P 37/06; A61P 37/08; A61P 17/02; A61P 17/04; A61P 17/06; A61P 17/08; A61P 17/10; A61P 17/12; A61P 17/14; A61P 17/16; A61P 17/18; A61P 19/02; A61P 19/08; A61P 19/10; A61P 1/16; A61P 21/00; A61P 23/00; A61P 25/00; A61P 27/02; A61P 29/00; A61P 31/18; A61P 35/04; A61P 37/02; A61P 7/00
See application file for complete search history.

(56) References Cited

OTHER PUBLICATIONS

Budesonide-beta-D-glucuronide: a potential prodrug for treatment of ulcerative colitis, Nolen, H., 3rd, Fedorak RN, Friend DR, J.Pharm Sci, Jun. 1995.

Spacer/Linker Based Synthesis and Biological Evaluation of Mutual Prodrugs as Antiinflammatory Agents, V.S. Velingkar, D.R. Jain, D.C. Ahire, Indian Journal of Pharmaceutical Sciences, Sep.-Oct. 2010.

* cited by examiner

BUDESONIDE PRODRUG

BACKGROUND OF THE INVENTION

1. Field of the Invention

The present invention relates to compositions for the treatment of inflammatory intestinal diseases.

2. Brief Summary of the Prior Art

Controlled release pharmaceutical composition including budesonide for treatment of conditions such as inflammatory bowel disease, irritable bowel syndrome, and Crohn's disease are known. For example, U.S. Patent Publication 2015/0118296 A1 discloses a controlled release pharmaceutical composition including a tablet core including budesonide, an amphiphilic excipient, a hydrophilic excipient, and one or more pharmaceutically acceptable excipients, covered with a coating comprising a gastro-resistant film. U.S. Pat. No. 9,707,182 B2 discloses a sustained release pharmaceutical dosage form of budesonide having an inert core, a first sustained release matrix layer including budesonde, sugar and a water-insoluble polymer such as ethyl cellulose, and a second delayed release film coating including acylic acid and methacrylic acid esters.

Inflammatory bowel disease (IBD) is a collection of inflammatory conditions of the colon and the small intestine. The principal forms of IBD are Crohn's disease and ulcerative colitis (UC), characterized by recurrent occurrences of serious mucosal injury and inflammation. Presently, there are no precise drugs available, and IBD medication relies primarily on non-steroidal anti-inflammatory drugs (NSAIDs), glucocorticosteroids, and immunomodulators. With the present recommended remedies for IBD, only 80% of the patients seem to receive slight relief from issues of inflammation and accompanying symptoms. The primary goal of drug therapy is to decrease colonic inflammation that requires frequent ingestion of NSAIDs and glucocorticosteroids at elevated doses, which might result in augmented occurrence of gastrointestinal ulceration, bleeding and other complications. The pathogenesis of IBD still remains unclear. Numerous studies on the etiology of IBD have shown that the diseases are the result of insufficiently suppressed immune response.

Colon-specific drug delivery (CSDD) has evolved out of the necessity to overcome the barrier of the gastrointestinal tract, as an ideal delivery system for the treatment of IBD. The prodrug approach is one of the several promising tools for targeting drugs to the colon. CSDD through colon-specific prodrug activation may be accomplished by exploiting the high activity of certain enzymes at the target site compared with non-targeted tissues for conversion of the prodrug to active drug. Patents related to colon targeted prodrug approach include time explosion method, multiparticulate galenic forms, cytidine analogues, minicapsules, polymeric materials in combination with saccrides, selective serotonin reuptake inhibitor, pH dependent polymers, and hydrogels.

Oral and intravenous use of glucocorticosteroids are restricted in patients with UC because of adrenosuppression, osteoporosis, immunosuppression. Though rectal administration is being favored, however, increased doses may lead to side effects. Budesonide is a glucocorticosteroid (poor aqueous solubility) used in the treatment of IBD. It works by decreasing inflammation in the digestive tract of people who have IBD. Studies have shown that the budesonide prodrug is successful in reducing colitis induced experimentally in rats.

The size of the molecule plays an important role in diffusivity of a drug. Generally, biodisposition, localization and transit of a drug are controlled by particle characteristics such as size, shape and charge. Usually, the prodrug approach increases the size of the molecule. However, no studies have reported a negative effect of the prodrug approach to diffusivity, primarily because the size may not have been excessively large.

Budesonide prodrugs are known. For example, budesonide-beta-D-glucuronide is known to accelerate the treatment of colitis in rats. H. Nolen 3d, *J. Pham. Sci.* 1995 84(6), 677-81.

There is a continuing need for compositions and methods for use in the treatment of patients suffering from inflammatory bowel disease including Crohn's disease and ulcerative colitis, and in particular for compositions deliverable in effective and affordable dosage forms.

SUMMARY OF THE INVENTION

The present invention provides a prodrug for treatment of bowel diseases including irritable bowel syndrome, ulcerative colitis and Crohn's disease, the prodrug having the structure of Formula I below:

Formula I

The present invention also provides a pharmaceutically effective composition including a prodrug according to Formula I. The present invention also provides a pharmaceutically effective composition including a prodrug according to Formula I and a colon-specific drug delivery system. In addition, the present invention provides a pharmaceutically effective composition including a nano-precipitated prodrug according to Formula I.

Further, the present invention provides a pharmaceutically effective composition including a prodrug according to Formula I dispersed in an asymmetric membrane-in-membrane capsule. In one aspect, the present invention provides a pharmaceutically effective composition including a prodrug according to Formula I wherein the asymmetric membrane-in-membrane capsule is formulated to provide a normal drug release profile. In another aspect, the present invention provides a pharmaceutically effective composition including a prodrug according to Formula I wherein the asymmetric membrane-in-membrane capsule is formulated to provide a delayed drug release profile.

Preferably, a pharmaceutically effective composition of the present invention includes a prodrug according to Formula I having a volume average particle size less than about 1000 nm. Preferably, a pharmaceutically effective composition according to the present invention includes a prodrug according to Formula I having a volume average particle size from about 100 nm to 300 nm prior to agglomeration of the prodrug.

In addition, the present invention also provides a method of treating a bowel disease in a patient, the method comprising administering to the patient a therapeutically effective amount of a pharmaceutically effective composition including a prodrug having the structure of Formula I. In one aspect the method of the present invention provides a pharmaceutically effective composition according to Formula I including a colon-specific drug delivery system. Preferably, the prodrug employed in the method is nano-precipitated.

Preferably, the prodrug is dispersed in an asymmetric membrane-in-membrane capsule. In one aspect, the asymmetric membrane-in-membrane capsule employed in the method is formulated to provide a normal drug release profile. In another aspect, the asymmetric membrane-in-membrane capsule employed in the method is formulated to provide a delayed drug release profile. Preferably, the prodrug employed in the present method has a volume average particle size less than about 1000 nm, and more preferably from about 100 nm to 300 nm prior to agglomeration of the prodrug.

In another aspect, the present invention provides a drug delivery system comprising:

a) an asymmetric membrane-in-membrane capsule including a first membrane having an average pore size of no greater than a first average size;

b) a prodrug having the structure of Formula I, the prodrug when dissolved in the fluid medium having an average particle size less than the first average size. Preferably, the first average size of the pore size is less than about 1000 nm, and more preferably, from about 100 nm to 300 nm.

DETAILED DESCRIPTION

The present invention provides a nano prodrug, as well as a method of deliverying the nano prodrug to the colon, and the release of the prodrug in a controlled fashion. The method provides for a system which maintains its integrity throughout the gastrointestinal tract. The phase transited capsules of the present invention involve phase inversion in a polymeric system for formation of the capsules. Phase inverted capsules for use in the present invention can be fabricated by different methods for either normal drug release profile or delayed release. The asymmetric membrane capsules preferably employed in the process of the present invention are believed to have a good in vitro to in vivo relationship. These capsules can be prepared by a known method.

The present invention provides a nano prodrug of budesonide (BuP) to reduce the side effects of budesonide (Bu), and achieve controlled site targeting. The BuP can be prepared in two phases by nano precipitation. Preferably, the delivery system includes an asymmetric membrane-in-membrane capsule (AMMC) made though phase transition. The BuP can be characterized for their shape and size and their formation through Fourier transform infrared spectroscopy (FTIR), mass spectroscopy, nuclear magnetic resonance spectroscopy, differential scanning calorimetry, and scanning electron microscopy. The AMMCs can include an outer dense non-porous region and an inner light porous region, with pores in the nano range.

Drug release can be evaluated using a factorial design. The effects of different formulation variables and osmotic pressure on drug release can be studied. Different kinetic models can be applied to understand the drug release from the AMMCs.

Budesonide-glycine nano prodrug was prepared by a nano precipitation method. The nano prodrug was synthesized in two phases. Phase 1 involved formation of budesonide BOC-Glycine complex, and Phase 2 involved removal of BOC to form the budesonide-glycine nano prodrug.

A mixture of N-(tert-butoxycarbonyl) glycine (3.084 g, 4.4 mmol) and dicyclohexylcarbodiimide (DCC, 6.168 g, 2.6 mmol) in dry methylene chloride (30 ml) was mixed at room temperature (under nitrogen) for 3 hours. The insoluble portion was filtered off, and the evaporation of the solvent was accomplished under vacuum. The resultant N-BOC-glycine was dissolved in dimethylformamide (DMF, 90 ml) and budesonide (1.16 g, 2.69 mmol) was added followed by 4-dimethylaminopyridine (DMAP, 146 mg, 0.12 mmol). The mixture was initially sonicated (20 KHz, 5 min.), and then stirred at room temperature for 48 hours. Intermittent sonication was provided. Vacuum was used to remove the solvent and a solvent system of chloroform-methanol (10:1) was used for chromatography of the crude product on a silica gel column used to give budesonide-N-BOC-glycine conjugate. A solution of budesonide-N-BOC-glycine (0.18 g, 0.31 mmol) in 5% HCl/ethyl acetate (45 ml) was stirred at room temperature for 1.5 hours at high speed with intermittent sonication. The homogenized mixture was separated into three parts. One part (as suspension) was directly put into a particle sizer to check for size and shape (Ocean Optics QE65 Pro, Florida, USA), the second pad was chromatographed on a silica gel column using $CHCl_3.MeOH$ (10:1). The third part was vacuum filtered, the particle washed with double distilled water three times, and immediately subjected to freeze drying for 24 hours using a freeze drier (LD Plus FD, Christ, Germany).

A phase inversion process was used to prepare AMMCs in two steps. In both the steps, the polymeric solutions were sonicated (20 KHz, 10 minutes) to achieve nano pored internal membranes. The sonication causes periodical compression and rarefactions when passing through the polymeric solutions. Therefore, a localized hotspot region of high temperature and pressure is created that breaks up aggregates of micron-sized colloidal particles (in the polymer). Sonicating the polymeric solution before phase inversion (i.e. sonication before making the capsule) provides nano-sized polymer particles. So the polymer-poor phase (glycerol-now as nanoparticle) being soluble in medium dissolved made a nano-pore on the surface of the capsule. In the first step, glass mold pins (diameter, 5.61±0.12 and 6.21±0.13 for the body and cap, respectively) were dipped into a mixture of 10% w/v and 15% w/v ethyl cellulose (EC) dissolved in 35% v/v acetone and 5% w/v and 10% w/v glycerol dissolved in 20% v/v and 15% v/v ethanol respectively. In the phase inversion process, there are two phases: polymer-rich and polymer-poor. The polymer-rich phase gets solidified into a solid matrix (capsule body) while the polymer-poor develops into pores on the capsule. The pore size and distribution can be adjusted by adjusting experimental conditions. For phase transition the pins were submerged in a quenching solution (glycerol, 10% w/v) for 10 minutes. The quenching was followed by a quick air drying of the film on the glass mold pins for 20 seconds. In the second step the air dried film on the mold pins was dipped into 15% w/v and 20% w/v CAP solution and 2.5% w/v and 5% w/v castor oil dissolved in a 35% v/v acetone and 20% v/v and 15% v/v ethanol respectively. This was followed by quenching in castor oil (10% w/v) for 5 minutes. The second quenching process was followed by 20 seconds of air drying. The films formed on the glass mold pins were removed off the pins, trimmed to size (to resemble a capsule), and kept in a desiccator until further use. AMMCs were manually filled with a BuP (9 mg) and mannitol (25 mg) by mixing in a bag for 5 minutes. The AMMCs were capped and sealed with 10% w/v EC in a mixture of acetone and alcohol.

The release of the drug is controlled by the pores present in the capsule. If the pores are very big then more dissolution medium will enter the capsule and more drug will be released (difficult to have controlled release). If the pore size is small (preferably ~200 nm), then the release of the drug particles inside the capsule (~150-180 nm) can be controlled.

The composition of AMMC as per a $2^3$ factorial design is given in Table 1.

membrane hydrophobicity and protect the AMMC. When the capules are exposed to the alkaline environment of the intestine, the CAP dissolves so the inner coat is exposed. An Inner layer includes EC with and glycerol (primary ingredients). EC does not dissolve in the GI tract. However, glycerol is hydrophilic and dissolves, thereby leaving pores (nano-sized) on the EC coated AMMC (asymmetric membrane capsule). Sonication of the coating composition helps in the creation of the nanopores on the membrane.

To study the drug content, a hundred milliliters of phosphate buffer (along with rat fecal content) was prepared, and 10 mg of prepared BuP was crushed and added to it. The mixture was sonicated at 10 kHz for 5 minutes. Fiber optic probes were inserted into the sample solution, and readings taken at 232 nm using the fiber optics system. The experiment was conducted in triplicate.

Solubility studies of the pure Bu and prepared BuP were determined (n=6) by making saturated solutions of HCl buffer, phthalate buffer, phosphate buffer of pH 1.2, 4.0, 6.8 (with and without 10% w/v rat fecal content), and 7.4 respectively. The solutions, kept separately in a conical flask, were subjected to ultrasonic waves in an ultrasonic bath (Sonorex, Bandelin Electronic, Germany) for 30 minutes. Fiber optic probes were inserted at 0 and 30 minutes, and readings taken at 232 nm for Bu and 340 nm for BuP using the fiber optics system Reversed phase TLC was used for $R_M$ value (n=6) determination. Silica gel GF254 TLC plates were dipped in acetone containing n-octanol (3% v/v) for 5 hours, and dried overnight. Five µL (sample spot) of Bu and BuP solution was marked at a distance of 2 cm intervals. An ascending technique was used (under equilibrium conditions) for development of the compound spot in the chromatographic chamber. A mobile phase of methanol/chloroform/water in a ratio of 14:1:5%, v/v/v was used. The TLC plates, after drying, were analyzed for the compound spot under UV fluorescence cabinet at short wavelength 254 nm. The Rf value (n=6) was determined for the compound, and the relative RM values calculated by the formula:

$$R_M = \log(1/Rf - 1) \tag{Equation 1}$$

The Hansch method was used to determine the partition coefficient between the n-octanol and phosphate buffer (both

TABLE 1

| Sample | Variable | AMMC | | | | | | | | |
|---|---|---|---|---|---|---|---|---|---|---|
| | | F1 | F2 | F3 | F4 | F5 | F6 | F7 | F8 | F9 |
| 1 | budesonide prodrug (mg) | 9 | 9 | 9 | 9 | 9 | 9 | 9 | 9 | 9 |
| 2 | ethyl cellulose (% w/v) | 15 | 15 | 10 | 15 | 10 | 10 | 15 | 15 | 10 |
| 3 | mannitol (mg) | 25 | 25 | 25 | 25 | 25 | 25 | 25 | 25 | 25 |
| 4 | glycerol (% w/v) | 5 | 10 | 5 | 10 | 5 | 10 | 10 | 5 | 10 |
| 5 | cellulose acetate phalate (% w/v) | 20 | 15 | 20 | 20 | 15 | 15 | 20 | 15 | 20 |
| 6 | castor oil (% w/v) | 2.5 | 5 | 2.5 | 5 | 2.5 | 5 | 2.5 | 2.5 | 5 |
| 7 | glycerol for quenching (% w/v) | 10 | 10 | 10 | 10 | 10 | 10 | 10 | 10 | 10 |
| 8 | quenching time (min.) | 20 | 20 | 20 | 20 | 20 | 20 | 20 | 20 | 20 |
| 9 | castor oil for quenching (% w/v) | 10 | 10 | 10 | 10 | 10 | 10 | 10 | 10 | 10 |
| 10 | acetone (% v/v) | 35 | 35 | 35 | 35 | 35 | 35 | 35 | 35 | 35 |
| 11 | ethanol (95%) (% v/v) | 20 | 15 | 20 | 15 | 20 | 15 | 15 | 20 | 15 |
| 12 | water (mL) | Qs | Qs | Qs | Qs | Qs | Qs | Qs | Qs | Qs |

Thus, the AMMC comprises two coats. An outer layer serves to protect the system from releasing the drug in the gastric medium. This layer includes cellulose acetate phthalate (CAP) andh castor oil (primary ingredients) that give the 10 mL) system. Different pH systems of 1.2, 4.0, 6.8, and 7.4, and n-octanol and double distilled water (both 10 mL, pH 5.8) were prepared. The buffers, n-octanol, and double distilled water were added to a separating funnel. The phases were shaken for 60 minutes. to attain saturation. Ten milligrams of Bu and BuP were added to respective separators and were given 30 minutes of shaking for the drug to achieve sufficient distribution in both the phases. The separators were kept still for 5 minutes, and then the phases were separated. The phases were suitably diluted and analyzed (n=6) using the fiber optics with the UV detector set at 232 nm and 340 nm for Bu and BuP, respectively.

The differential scanning calorimetry (DSC) profile of the pure drug (Bu) and its physical mixtures were recorded on a Q20 calorimeter (TA Instruments, USA). Normal conditions were used to study the thermal behaviors using Hermetic Aluminum Pans (nitrogen flow of 50 mL/min). The samples (5.1 mg for pure Bu, 5.5 mg for EC, and 7.5 mg for Bu:EC (1:1), were heated at 10° C./min over a temperature range of 20-100° C., 0-250° C., and 20-180° C., respectively. In another experiment, mannitol samples (5.5 mg for pure mannitol, 9.7 mg for Bu:EC:mannitol) in 1:1:1 ratio were heated at 10° C./min over a temperature range of 0-250° C. Empty Hermetic Aluminum Pans were used as a reference sample in all three determinations. Peak temperatures were noted and reported.

Scanning electron microscopy provided detailed information about the sample including external morphology (texture), chemical composition, and crystalline structure and orientation of materials making up the sample. The samples were examined for their porous inner structure and a non-porous outer structure using a JSM-6510LA scanning electron microscope (Jeol, Japan). The samples were mounted on a 10 mm×10 mm aluminum stub by sticking the membrane on double-sided carbon adhesive die. The mounted samples were then sputter coated for 3-5 minutes with platinum by using an auto fine coater (JFC-1600, Jeol, Japan), and examined using SEM.

FT-IR of the pure Bu and BuP were recorded on Bruker IR spectrometer (Spectrum, Bruker, USA). Samples were prepared in KBr disc (about 10 mg sample for 100 mg of dry KBr). The IR spectra were obtained in the spectral region 450-4000 cm$^{-1}$.

A Waters Quattaro Premier XE Tandem quadrupole mass spectrometer (Waters Corporation, Milford, Mass., USA) was used to accomplish mass analysis of pure Bu and BuP.

$^1$H NMR spectra and $^{13}$C of Bu, BOC-glycine conjugate, and BuP were recorded in a Brucker ASCEND-600 MHz Spectrometer (Brucker BioSpin AG, Switzerland). Deuterated chloroform (CDCl$_3$) was used as solvent.

BuP reversion was studied in many buffer media. This included HCl buffer, phthalate buffer, phosphate buffer of pH 1.2, 4.0, 6.8 (with and without 10% w/v rat fecal content), and 7.4 respectively. All the buffer media were maintained at 37±0.5° C. The amount of potassium chloride was adjusted to maintain the ionic strength (p=0.5). 72 BuP was dissolved in buffer mediums to achieve a concentration of 1000 μg/mL. One milliliter of this BuP solution was diluted (10 mL) in glass vials with the respective buffers to give a final concentration of 100 μg/mL. Five milliliter of the solution was taken from the glass vials at varied intervals and mixed with n-butanol (equal amount) to extract free Bu reverted from BuP. The Bu concentration was analyzed (n=6) from the n-butanol layer using the fiber optics system with a UV detection at 232 nm.

The drug release was studied from the prepared formulation using a standard USP type II apparatus. The conditions used were a rotating speed of 100 rpm, temperature of the dissolution media of 37°±0.5° C. A modified method A was used for studying the drug release at different periods. Briefly, for the first 2 hours, 0.1 N HCl (pH 1.2, 750 mL) was used as simulated gastric fluid, SGF, followed by tribasic sodium phosphate (0.20 M, 250 mL) addition to create "simulated intestinal fluid" ("SIF"). The addition of tribasic sodium phosphate was after it was equilibrated to 37±0.5° C. The pH of the SIF was adjusted to 6.8 with 2 N NaOH. The whole process took about 3.5 minutes. Fresh rat fecal contents were added after a total of an 8-hour study to mimic colonic environment. The sample (5 mL) was withdrawn at specified intervals, suitably diluted and analyzed at 232 nm and 340 nm using fiber optics.

The effect of changing osmotic pressure on Bu release was studied using the best formulation (n=6) in a media having different osmotic pressures. Different concentrations of mannitol was added to the dissolution medium (SIF), pH 6.8 with rat fecal content to create different osmotic pressures. USP dissolution apparatus was used for the experiment using 1000 mL of the dissolution media at a temperature of 37°±0.5° C. The paddle rotation speed was set to 75 rpm. A different type of analysis method (Residual Analysis Method) was used. This method was used to minimize the chance effect of any interaction between Bu and mannitol. At designated time intervals, the formulation (undergoing dissolution) was removed and cut open. The contents were allowed to dissolve in 250 mL SIF. The residual amount in each asymmetric membrane capsule was determined by taking 1 mL of the sample, suitably diluting, and analyzing at 232 nm using the fiber optics system.

The drug release kinetics from a controlled release formulation can be studied by applying various mathematical models. The best models applied are: The zero order rate (Equation 2), first-order equation (Equation 3), Higuchi model (Equation 4), Hixson-Crowell cube root law (Equation 5), and Peppas and Korsmeyer equation (Equation 6).

$$Q_t = k_0 t \qquad \text{(Equation 2)}$$

$$\ln Q_t = \ln Q_o k_1 t \qquad \text{(Equation 3)}$$

$$Q_t = k_H t^{1/2} \qquad \text{(Equation 4)}$$

$$Q_o^{1/3} - Q_t^{1/3} = k_{HC} t \qquad \text{(Equation 5)}$$

$$M_t / M_\infty = k t^n \qquad \text{(Equation 6)}$$

where the drug initial amount in the formulation is represented by $Q_o$, the drug amount released at time (t) is represented by $Q_t$. Rate constants (release) for zero order, first-order, Hixson-Crowell, Higuchi model, are represented by $k_0$, $k_1$, $k_{HC}$, and $k_H$ respectively. The drug amount released at time t and $\infty$ are represented by $M_t$ and $M_\infty$ respectively. The kinetic constant and diffusional coefficient are represented by k and n respectively. The residual sum of squares (SSQ) and goodness of fit were taken as basis for selecting the best release profile.

Statistical analysis was performed using GraphPad InStat Software (Version 3.00; Graph Pad Software, San Diego, Calif., USA) with one-way ANOVA, a p<0.05 was considered statistically significant.

The FTIR, NMR and MS results showed the purity of the drug sample, and identified the drug as budesonide. FT-IR (KBr): 3483.89 cm−1 (OH stretching), 1722.06 cm−1, 1664.42 cm−1, 1624.49 cm$^{-1}$ (stretching of different C=O groups). $^1$HNMR (600 MHz, CDCl$_3$): δ 7.23-7.21 (m, 1H), 6.26-6.23 (m, 1H), 6.00-5.99 (m, 1H), 5.15-5.12 (m, 2H), 4.87-4.86 (m, 1H), 3.01-2.99 (m, 1H), 2.56-2.51 (m, 2H), 2.33-2.30 (m, 1H), 2.16-2.04 (m, 3H), 1.63-1.53 (m, 5H), 1.42 (s, 3H), 0.90-0.86 (m, 3H). $^{13}$C NMR (MHz, CDCl3): δ 210.11 C20, 186.48 C3, 169.64 C10, 155.8 C1, 127.97 C2, 122.55 C4, 108.35 C17, 104.6 0 C22, 83.35 C16, 69.95 C11, 67.23 C21, 55.18 C8, 43.93 C13, 41.29 C9, 40.96 C14, 37.04 C23, 34.93 C7, 33.94 C5, 32.94 C15, 30.99 C6, 21.06 C18, 17.68 C19, 13.93 C24, 13.93 C25. ESI-MS (100% methanol) 452 (M+ Na), 413 (M− OH).

The drug solution showed a maximum wavelength ($\lambda$max) of 232 nm, and an absorbance value of 1.658±0.01 in phosphate buffer, pH 7.4. Freshly prepared solutions were used to make calibration curves in a range of 0-30 mg/mL. The study was conducted consecutively for three days to study the standard curve's reproducibility. A value of 0.01% for the precision value coefficient of variation (CV) suggested a high reproducibility of the standard curve. A high level of correlation observed between the absorbances and respective concentrations ($R^2$=0.9998) suggested linearity of the regressed line. The suggestion was supported by the linearity test. The test was applied to confirm if the regressed line was a curve or a straight line. A p value (0.3212±0.0130) revealed a perfect linearity for the line (regressed) at 95% confidence interval.

A Cilas particle sizer and shape analyzer was used to characterize BuP. The particle size of the suspension immediately after preparation and after freeze drying (resuspended in water) was observed using the wet samples. The shape analyzer showed the spherical nature of the resuspended freeze dried BuP. The analyzer did not detect any samples less than 500 nm. Differences in particle size were found for the BuP analyzed after the ultrasonication, and the freeze dried product. Ultrasonication resulted in particle size in the range of 150-230 nm with the maximum falling in this range (87%). The particle size of the freeze dried products was around 480-600 nm. The increase in the sizes of the freeze dried product can be attributed to agglomeration during the process as compared to the suspension analyzed immediately after the ultrasonification.

The drug content of the prepared formulations were found to be 96.78%±1.67%. Table 2 presents the solubility (aqueous) and partition coefficient of Bu and BuP in various buffer media. Aqueous solubility of Bu and BuP increased with increasing pH with the maximum reaching, in phosphate buffer, pH 7.4. The reason is believed to be increased ionization and presence of polar groups of Bu and BuP respectively in relation to the increase in pH of the buffer mediums. No changes were found in the solubility of Bu in phosphate buffer, pH 6.8 with and without fresh rat fecal content (10% w/v), suggesting that the absorbance for Bu is not affected by the rat fecal content. The increased solubility of BuP than Bu can be attributed to the polar glycine moiety, which increases the polarity of the BuP much more than the less polar Bu. The increased log P values suggested statistically negligible lipophilic character at 95% confidence interval (p=0.4653±0.0732). The negligible increase in the lipophilic character was due to the glycine moiety. The results were supported by the $R_M$ values, which were proportional. $R_M$ values for BuP and Bu were −0.301±0.036 and −0.478±0.076 respectively. This suggests that BuP is slightly more lipophilic than Bu.

Figure 1:
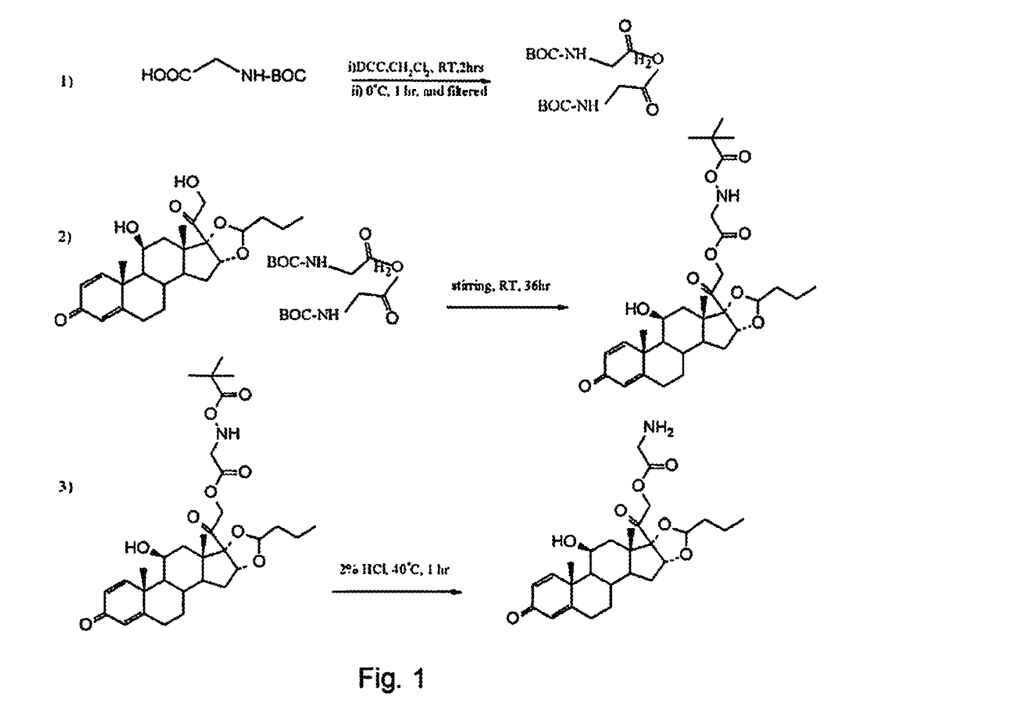
FIG. 1 is a schematic representation of the synthesis of a budesonide prodrug according to the present invention.
Figure 2:
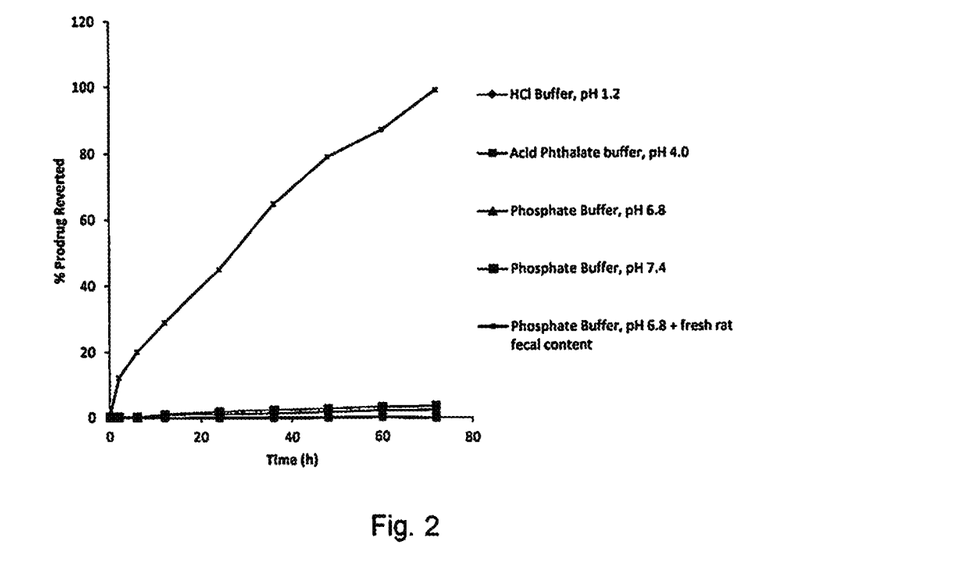
FIG. 2 is a plot showing the in vitro reversion of BuP to Bu in different buffers and pH and in a colonic medium.

The in vitro reversion studies (n=6) involved determining the amount of Bu reverted from BuP. Reversion studies (FIG. 2) confirmed that BuP reversion was negligible in SGF (HCl buffer, pH 1.2, and acid phthalate buffer, pH 4.0), and SIF, only 2.30±1.21% in phosphate buffer, pH 6.8 and 3.53±2.13 in phosphate buffer, pH 7.4 over a period of three days. Thus, the aim of circumventing the GIT without the release of free drug was achieved. Furthur reversion studies in phosphate buffer, pH 6.8 in the presence of rat fecal matter (10% w/v) confirmed the colonic breakdown of BuP. In colonic conditions (simulated) over 98.98±1.52% of BuP was reverted to Bu. The presence of fecal matter (colonic microflora) might have initiated a catalytic hydrolysis of BuP in the presence of amidase enzyme thereby resulting in increased reversion.

TABLE 2

| | Solubility (μg/mL) | | | | Log P | |
|---|---|---|---|---|---|---|
| | Bu | | BuP | | | |
| | 0 min | 30 min | 0 min | 30 min | Bu | BuP |
| Hcl buffer, pH 1.2 | 25.10 ± 1.43 | 88.12 ± 0.67 | 41.23 ± 2.51 | 123.01 ± 2.51 | 3.12 ± 0.12 | 4.01 ± 0.43 |
| Phthalate buffer, pH 4.0 | 68.15 ± 0.98 | 148.01 ± 1.32 | 85.32 ± 1.83 | 203.11 ± 1.91 | 3.01 ± 0.54 | 3.24 ± 0.98 |
| Double distilled water, pH 5.8 | 121.09 ± 1.26 | 209.03 ± 2.13 | 165.32 ± 2.11 | 302.33 ± 2.19 | 2.87 ± 1.05 | 3.05 ± 0.79 |
| Phosphate buffer, pH 6.8 | 187.28 ± 1.98 | 356.88 ± 0.99 | 225.12 ± 0.89 | 431.19 ± 1.54 | 2.51 ± 0.36 | 2.51 ± 1.09 |
| Phosphate buffer, pH 6.8 + rat fecal content | 187.09 ± 0.89 | 356.88 ± 1.76 | | | | |
| Phosphate buffer, pH 7.4 | 231.02 ± 2.12 | 476.12 ± 1.99 | 310.33 ± 2.11 | 579.21 ± 3.82 | 2.13 ± 1.09 | 2.20 ± 1.02 |

Data are mean ± SD (n = 6)

Figure 3:
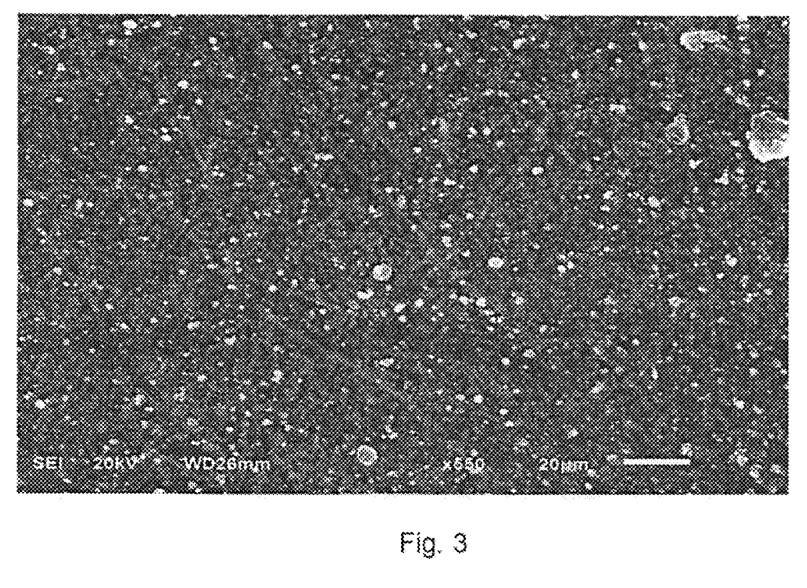
FIG. 3 is an electron micrograph showing an outer non-porous region of an asymmetric membrane-in-membrane capsule employed in the method of the present invention.
Figure 4:
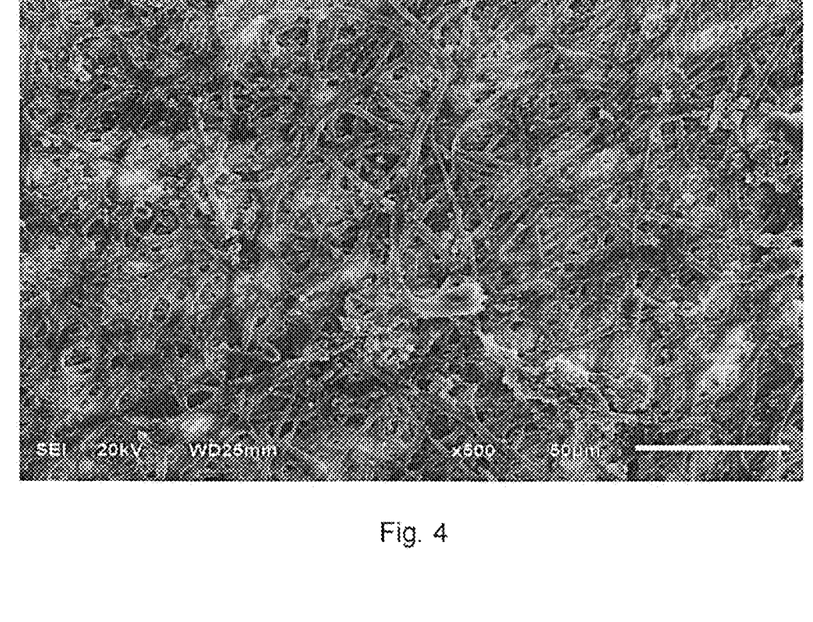
FIG. 4 is an electron micrograph of an inner porous region of the capsule of FIG. 3.
Figure 5:
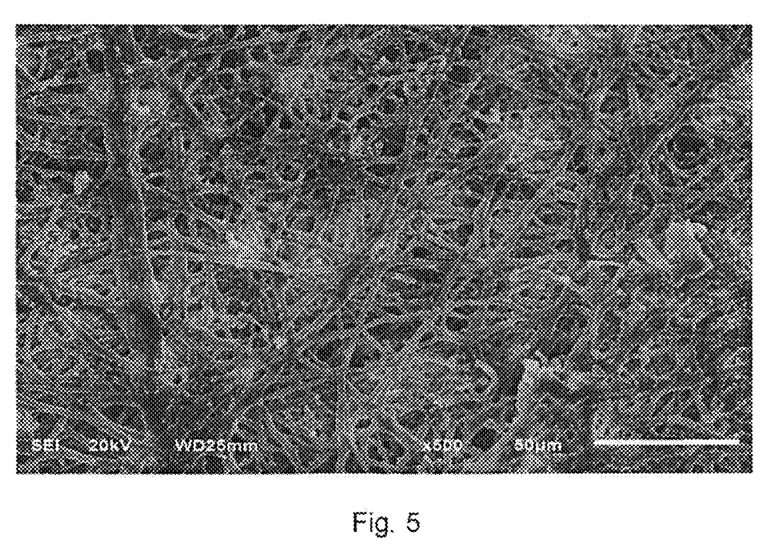
FIG. 5 is an electron micrograph of the inner membrane of the capsule of FIG. 3 after twelve hours of dissolution.
Figure 6:
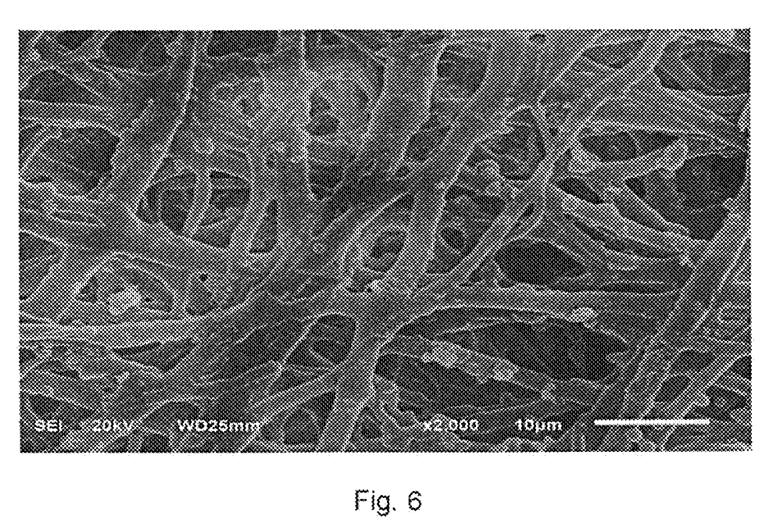
FIG. 6. is an enlarged portion of the electron micrograph of FIG. 5.

The SEM studies showed outer non-porous region for the AMMC (F1, FIG. 3), and a porous inner membrane (FIG. 4). FIG. 5, shows the condition of the inner membrane after 12 hours of dissolution. FIG. 6 represents the inner pore size at higher magnification.

Figure 7:
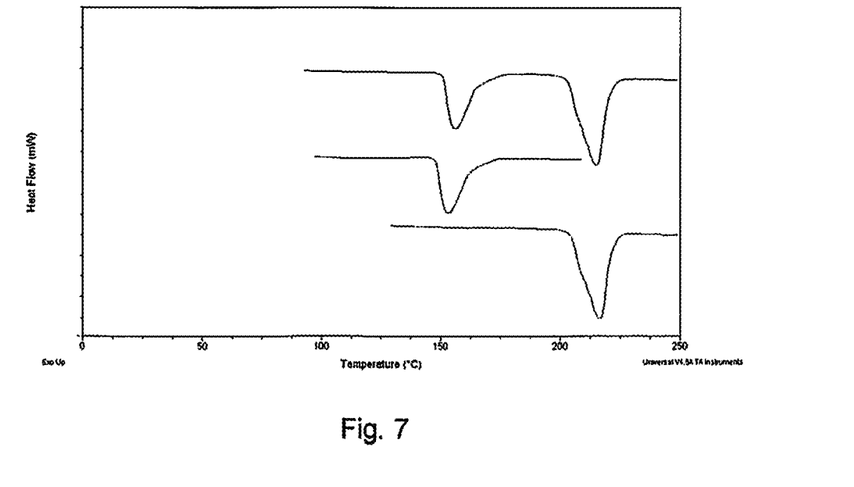
FIG. 7 is plot of heat flow versus temperature showing differential scanning calorimetry results for budesonide and ethyl cellulose.
Figure 8:
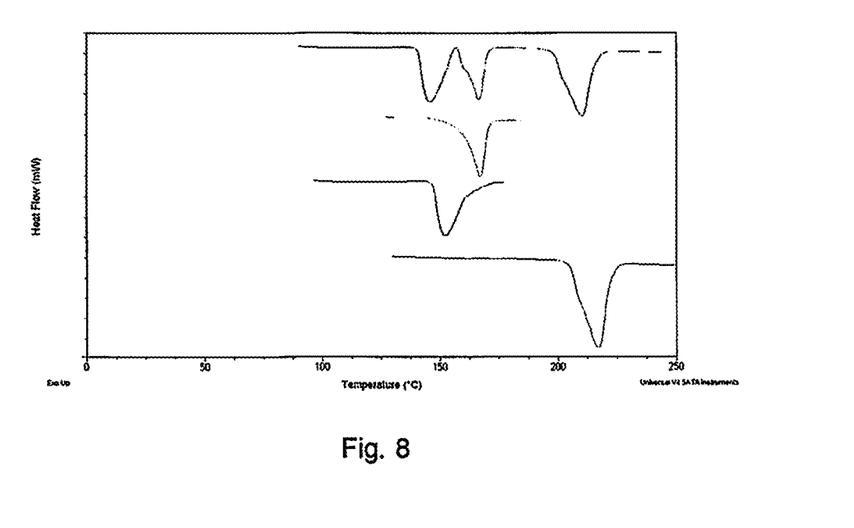
FIG. 8 is plot of heat flow versus temperature showing differential scanning calorimetry results for budesonide, ethyl cellulose and mannitol.

The thermal behavior of pure Bu and in mixture was investigated by heating the respective samples at 10° C./min. (FIG. 7). For the first sample (pure Bu) an endothermic peak was observed at 215±0.21° C. with an enthalpy of 144.1±2.11 J/g. The second sample (EC) had an endothermic peak at 152.1±0.41° C. with an enthalpy of 98.14±1.23 J/g. The third sample (Bu: EC) had two endothermic peaks at 215±0.31° C. and 151.91±0.13° C. with an enthalpy of 141.20±0.71 J/g and 97.18±2.12 J/g respectively. The inclusion of mannitol in the mixture formulation is represented in FIG. 8. Mannitol showed an endothermic peak at 160.23±0.21° C. with an enthalpy of 103.43±1.21 J/g alone, and 161.13±0.32° C. with an enthalpy of 101.23±1.10 J/g in the triple mixture of Bu and EC. Both Bu and EC showed a very slight shift due to the presence of hydrophilic mannitol. These were 211±0.54° C. with an enthalpy of 139.31±0.98

J/g 149.41±0.54° C. with an enthalpy of 97.19±2.31 J/g. This again demonstrated there was no interaction between the drug and excipient used.

Each of the FTIR, NMR and mass spectroscopic analytical techniques helped in identification of the formed BuP. The three studies were combined to help understand the formation of Bu-BOC-glycine and BuP respectively.

FTIR (KBr) 3323 cm$^{-1}$ (NH stretching of amide group), 2117 cm$^{-1}$ (N—C=O group), 1701 cm$^{-1}$, 1660 cm$^{-1}$, 1624 cm$^{-1}$ (C=O groups), 1269 cm$^{-1}$ (C—O), 1241 cm$^{-1}$ (C—O), 1184 cm$^{-1}$ (C—O), 1158 cm$^{-1}$ (C—O) $^1$HNMR (600 MHz, CDCl$_3$): δ 7.98 (s, 1H), 6.25-6.22 (m, 1H), 5.99-5.96 (m, 2H), 4.89-4.87 (m, 1H), 4.28-4.25 (m, 2H), 3.8-3.80 (1H), 1.71 (s, 9H). $^{13}$CMR (MHz, CDCl$_3$): δ 201.8 C20, 186.5 C3, 169.7 C26, 168.4 C10, 158.4 C1, 156.2 C28, 1287.9 C2, 122.5 C4, 108.3 C17, 104.6 C22, 84.8 C16, 79.7 C29, 69.8 C11, 68.1 C21, 55.3 C8, 43.98 C13, 43.96 C9, 43.7 C14, 41.4 C27, 40.7 C12, 36.5 C23, 34.9 C7, 32.87 C5, 32.5 C15, 31.8 C6, 27.94 C30, 21.04 C18, 17.5 C19, 16.9 C25, 13.9 C24. ESI-MS (100% methanol) 610 (M+ Na, 27.0), 471.08 (M- C$_5$H$_{10}$NO$_2$), 246.7 (M- C$_{11}$H$_{15}$NO$_5$, 100).

FT-IR (KBr) 3400-3300 cm$^{-1}$ (NH$_2$), 2924 cm$^{-1}$, 2852 cm$^{-1}$ (CH$_3$), 1653, 1610, 1558 cm$^{-1}$ (C=O), $^1$HNMR (600 MHz, CDCl$_3$): δ 6.3-6.2 (m, 2H), 5.99 (s, 1H), 5.28 (s, 2H), 4.29 (t, 1H), 3.21-3.20 (m, 2H), 1.90-1.88 (m, 2H), 1.61-1.59 (m, 2H), 1.43-1.41 (m, 2H), 0.87-0.84 (m, 3H). $^{13}$CMR (MHz, CDCl$_3$): δ 186.73 C3, 155.98 C1, 122.35 C4, 104.37 C22, 49.17 C8, 44.23 C27, 33.93 C14, 33.38 C5, 33.22 C12, 31.91 C6, 29.64 C12, 25.59 C4, 20.99 C18, 17.08 C25, 14.11 C24. ESI-MS (100% methanol): 471 (M$^+$-NH$_2$, 20), 430 (M −59), 305 (M- C$_8$H$_6$NO, 14.5), 446 (M- C$_3$H$_5$, 7.0), 246.7 (M- C$_{11}$H$_{15}$NO$_5$, 100).

Figure 9:
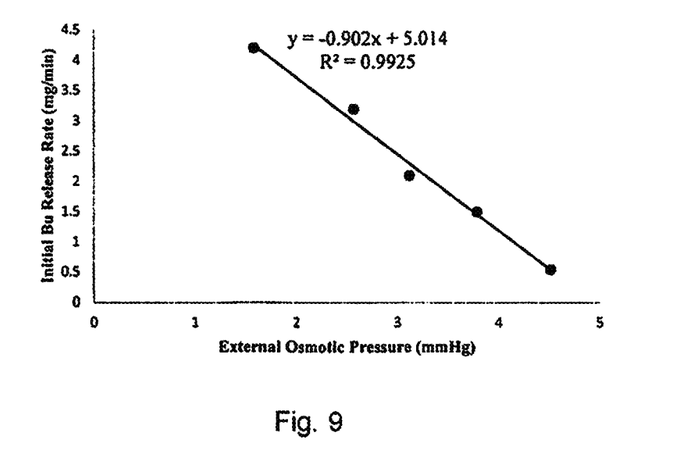
FIG. 9 is a plot of the initial budesonide release rate (mg/min.) versus external osmotic pressure (mm Hg).
Figure 10:
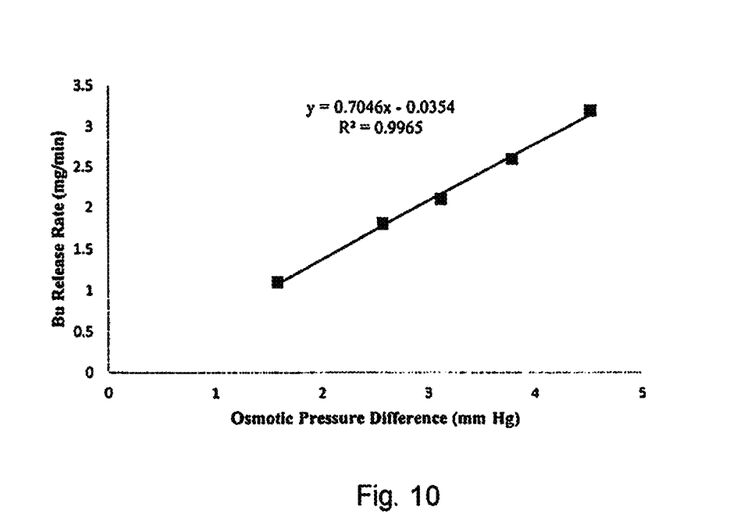
FIG. 10 is a plot of budesonide release rate (mg/min.) versus external osmotic pressure.

Osmotic pressure had an effect on the drug release. To study this effect, drug dissolution studies of the best formulation (n=6) were conducted in various osmotic pressure generated media (phosphate buffer, pH 6.8 with rat fecal content). Results indicated the dependent proportionality of drug release to the media's osmotic pressure. The release of Bu from AMMC (F1) reduced with an increase in the dissolution medium's osmotic pressures. A value of $R^2$=0.9925, suggested a linear relationship between the initial release rates and external osmotic pressure (FIG. 9). Similarly, a high degree of linear relationship ($R^2$=0.9965) between the release rate and osmotic pressure difference inside the formulation (FIG. 10) justified the relationship of osmotic pressure and drug release. Therefore, the conclusion that apart from the presence of enzymes (to revert the drug into Bu), the mechanism central for controlled drug release from the AMMC is osmotic pumping holds true.

Figure 11:
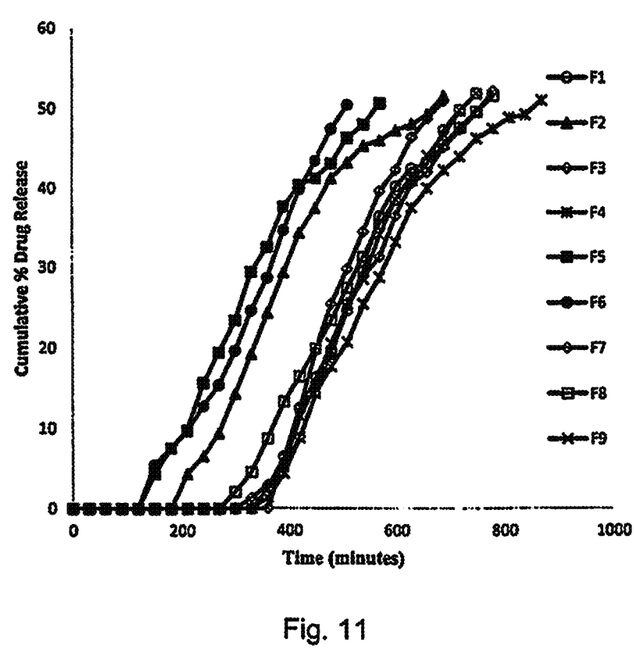
FIG. 11 is a plot of cumulative percent drug release versus time (dissolution profile) for various formulations.

Drug release studies were conducted as per $2^3$ factorial design (FIG. 11) with the creation of an extra design checkpoint formulation to study the drug release behavior as the formulation variables changed from one level to another individually and also during interactive studies. The response parameter was achievement of $t_{50\%}$. The order of achievement of $t_{50\%}$ was F6 (8.42±0.21 hours)>F5 (9.36±0.76 hours)>F2 (11.12±0.36 hours)>F3 (11.24±0.46 hours)>F1 (12.01±0.29 hours)>F7 (12.43±0.76 hours)>F8 (12.56±0.51 hours)>F4 (14.18±0.68 hours). Formulation F9 had a $t_{50\%}$ of 12.02±0.52 hours.

In all the formulation release studies, it was observed that as the pore size became wider and numerous, there was some release of mannitol (osmogen) into the dissolution media, thereby decreasing the osmotic pressure gradient, and reducing the release rate (as demonstrated in the osmotic pressure gradient study).

Furthermore, it was understood that initially, the pore size was smaller than the drug-complex/reverted drug size to inhibit their release, but gradually increased to be bigger than the reverted drug size to aid in their release.

The formulation F6 had the highest achievement of $t_{50\%}$ due to the fact that both the coating variables (EC and CAP) were at low levels, and the aqueous (glycerol) and non-aqueous (castor oil) plasticizers were at higher levels. This meant that the coating variable CAP quickly dissolved in the SIF due to its lower concentration and higher glycerol content, which was good, however the inner membrane (EC) developed too many pores with a larger radius due to higher castor oil content, thereby, initiating a release of the prodrug from the AMMC. The release of prodrug was confirmed by a negligible absorbance value at 232 nm (for Bu) and a high absorbance value at 340 nm (for BuP). The sudden presence of drug in the colonic environment was due to the fact the accumulated prodrug present in the non-colonic environment reverted to Bu. A high absorbance value at 232 nm and low absorbance value at 340 nm confirmed the above.

Formulation F5 had all the coating and pore forming variables at low level, which resulted in the release of the prodrug at a much earlier stage. The coating variables being in their low levels meant that the coating was not strong enough to delay the release into the colonic environment.

Formulation F2 also resulted in an early stage release of the prodrug. Although, the prodrug release at an early stage is not a problem per se, since it will only be reverted to Bu in the colonic region and be active, but it will cause an erratic dissolution/absorption behavior and will result in a varied dosing frequency.

Formulations F5, F6, and F2 were rejected because the $t_{50}\%$ was achieved way too early, which defeated the purpose of 12 hours release for 50% of the drug release. Formulation F3, achieved a $t_{50\%}$ of 11.24±0.46 hours. The formulation had only the enteric coating variable at a higher level and the pore formers at lower level, which helped in delaying the release of the prodrug until the colonic environment was created. However, the low concentration of the non-disintegrating polymer (EC) did not favor a higher $t_{50\%}$ in the $2^3$ factorial design study.

Formulation F7 had three of the four formulation variables at high level, but the non-aqueous plasticizer was at a lower level, which resulted in few pores being formed in the EC layer and delaying the 50% drug release beyond the 12 hours. The interactive study showed that although the aqueous polymer at higher concentration was good enough for faster pore formation, it did not prevent the early release of BuP in the SIF without the fecal content.

Formulation F8 had only the EC variable at a higher concentration and all others in lower concentrations. This probably resulted, as in the case of F7, in a delay in achievement of 50% drug in 12 hours.

Formulation F4 had all the variables at high level and therefore had the highest delay in achieving $t_{50\%}$ Formulation F1 had the coating variables at higher levels and pore formers at lower levels, which seemed ideal in achieving the $t_{50\%}$. Formulation F1 reached $t_{50\%}$ in 12.01 hours. Interactive study showed that although the EC and CAP were at high concentrations (could have led to decrease in the release), the low levels of pore formers were adequate to create holes on the release membrane, and help in release of reverted Bu from inside the AMMC. The nano pores on the membrane were responsible to hold the bigger prodrug complex in the system. Lysis took place only in the colonic environment, where the drug size was smaller than the membrane pores (at a later stage) and were released into the dissolution media. However, the lack of complete release in the gastric medium was due to the extra protection of a polymer that only dissolved in alkaline pH. There was a statistically negligible release in the phosphate buffer. The release may have been for the complex as some part of the membrane may have had bigger pores to contain the prodrug. The lysis could have been due to the alkaline pH.

As the study was statistically designed using a full factorial design, it needed to be validated by construction of an extra design checkpoint formulation. A polynomial equation that links the individual variables and the interactions in terms of effects was generated. The polynomial equation ($Yt_{50\%}$), which was reduced with significant coefficient values at a confidence level of 95% is given below:

$$Y_{t50\%} = {}_0 + B_1(X_1) + B_2(X_2) + B3(X_3)$$

where Y is the measured response; $B_0$ is the intercept; and $B_1$, $B_2$, $B_3$ are the significant coefficients calculated from responses at 95% confidence interval.

Figure 12:
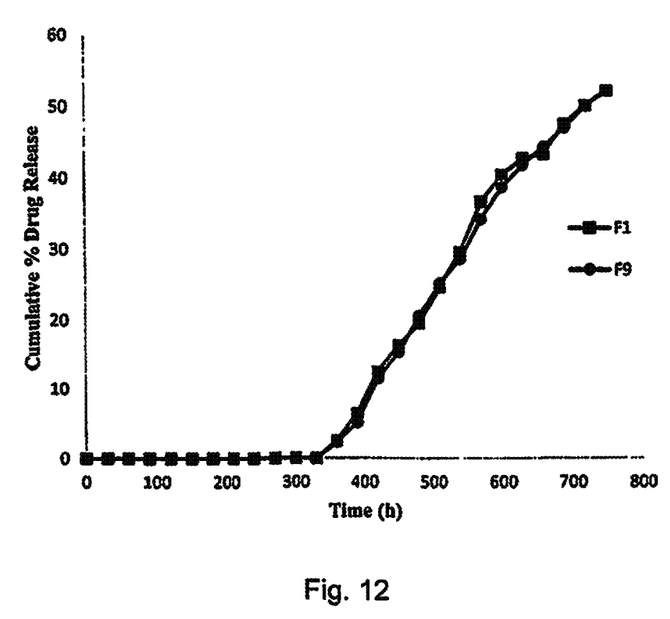
FIG. 12 is a plot of cumulative percent drug release versus time (dissolution profile) for formulations F1 and F9.

The predicted response for F9 calculated through Yates algorithm was 12.03 hours. The response of the extra design checkpoint actually was found to be 12.02±0.52 hours, which was very near. A $R^2$ value of 0.9997 between the observed and predicted values justified the design. The extra design checkpoint formulation F9 was compared with all the formulations in the design. The closest match with formulation F1 was justified with a similarity factor value, f2=98 (FIG. 12). Therefore, F1 was selected as the best formulation, and utilized for further studies.

All the formulations were subjected to release kinetic models (Table 3). Results showed that only F1 followed zero order model as the best-fit model along with F9. "Zero order" describes a case where drug release is concentration independent and is observed for poorly water-soluble drugs in matrix/transdermal, etc. "First-order" describes a drug release, which is concentration dependent and is observed for a water-soluble drug in porous matrix. "Higuchi model" describes drug release from an insoluble matrix, which is linearly related to the square root of time. "Hixson-Crowell model" describes drug release that depends on the surface area changes and particle/tablet diameter with time (applies to system which dissolves/erodes over time). Considering the higher correlation coefficient value (R) for both the F1 and F9 formulations, the release data seems to fit zero order model better. The drug release mechanism using the Power Law (F1: n=0.3212, k=0.5419, and R=0.9991; F9: n=0.4301, k=0.6781, and R=0.9998) confirmed that release of Bu reverted from BuP from F1 and F9 formulation, was Fickian diffusion

TABLE 3

| | | Formulations | |
|---|---|---|---|
| Kinetic Model | Parameters | F1 | F9 |
| Zero order | R | 0.9878 | 0.9989 |
| | SSQ | 121 | 431 |
| | $k_0$ | 0.0895 | 0.1253 |
| First-order | R | 0.9564 | 0.9671 |
| | SSQ | 65 | 216 |
| | $k_1$ | −0.0012 | −0.0014 |
| Higuchi | R | 0.9789 | 0.9881 |
| | SSQ | 189 | 43 |
| | $K_H$ | 1.5431 | 2.1431 |
| Hixson-Crowell | R | 0.9771 | 0.9231 |
| | SSQ | 74 | 380 |
| | $K_{HC}$ | −0.0086 | −0.0006 |

A nano prodrug of budesonide were successfully prepared and characterized. The prodrug showed an excellent reversion study data implying it would be effective in the colonic environment. The drug release data showed that the release was osmotic pressure dependent. The asymmetric capsular membrane-in-membrane system provided the necessary protection to the active pharmaceutical ingredient from the gastrointestinal fluids and delivered the drug in an effective manner to the colonic area. The delivery of nano prodrug to the colon using a phase transited capsular system appears to be a good way to achieve controlled release and to avoid the side effects of drugs.

Various modifications can be made in the details of the various embodiments of the compositions and methods of the present invention, all within the scope and spirit of the invention and defined by the appended claims.

The invention claimed is:

1. A prodrug for treatment of bowel diseases including irritable bowel syndrome, ulcerative colitis and Crohn's disease, the prodrug having the structure:

2. A pharmaceutically effective composition including a prodrug according to claim 1.

3. A pharmaceutically effective composition including a prodrug according to claim 1 and a colon-specific drug delivery system.

4. A pharmaceutically effective composition including a nano-precipitated prodrug according to claim 1.

5. A pharmaceutically effective composition including a prodrug according to claim 1 dispersed in an asymmetric membrane-in-membrane capsule.

6. A pharmaceutically effective composition including a prodrug according to claim 5 wherein the asymmetric membrane-in-membrane capsule is formulated to provide a normal drug release profile.

7. A pharmaceutically effective composition including a prodrug according to claim 5 wherein the asymmetric membrane-in-membrane capsule is formulated to provide a delayed drug release profile.

8. A pharmaceutically effective composition including a prodrug according to claim 1 wherein the prodrug has a volume average particle size less than 1000 nm.

9. A pharmaceutically effective composition according to claim 8 wherein the prodrug has a volume average particle size from 100 nm to 300 nm prior to agglomeration of the prodrug.

10. A method of treating a bowel disease in a patient, the method comprising administering to the patient a therapeutically effective amount of a pharmaceutically effective composition including a prodrug having the structure:

11. A method according to claim 10, the pharmaceutically effective composition including a colon-specific drug delivery system.

12. A method according to claim 10, the prodrug being nano-precipitated.

13. A method according to claim 10, the prodrug being dispersed in an asymmetric membrane-in-membrane capsule.

14. A method according to claim 13, the asymmetric membrane-in-membrane capsule being formulated to provide a normal drug release profile.

15. A method according to claim 13, the asymmetric membrane-in-membrane capsule being formulated to provide a delayed drug release profile.

16. A method according to claim 10 wherein the prodrug has a volume average particle size less than 1000 nm.

17. A method according to claim 16 wherein the prodrug has a volume average particle size from 100 nm to 300 nm prior to agglomeration of the prodrug.

18. A drug delivery system comprising:
   a) an asymmetric membrane-in-membrane capsule including a first membrane having an average pore size of no greater than a first average pore size;
   b) a prodrug having the structure:

wherein the prodrug when dissolved in a fluid medium has a particle size less than the first average pore size.

19. A drug delivery system according to claim 18, wherein the first average pore size is less than 1000 nm.

20. A drug delivery system according to claim 19 wherein the first average pore size is from 100 nm to 300 nm.

* * * * *

UNITED STATES PATENT AND TRADEMARK OFFICE
CERTIFICATE OF CORRECTION

PATENT NO. : 11,013,748 B2
APPLICATION NO. : 16/591940
DATED : May 25, 2021
INVENTOR(S) : Philip et al.

Page 1 of 1

It is certified that error appears in the above-identified patent and that said Letters Patent is hereby corrected as shown below:

In the Specification

Column 4, Line 51, "A" should start a new paragraph.

Column 4, Line 58, "pad" should be -- part --.

Column 7, Line 52, change "(p=0.5)" to -- ($\mu = 0.5$) --.

Signed and Sealed this
Twenty-ninth Day of June, 2021

Drew Hirshfeld
*Performing the Functions and Duties of the
Under Secretary of Commerce for Intellectual Property and
Director of the United States Patent and Trademark Office*